(12) United States Patent
Wang et al.

(10) Patent No.: US 6,475,179 B1
(45) Date of Patent: Nov. 5, 2002

(54) TISSUE FOLDING DEVICE FOR TISSUE ABLATION, AND METHOD THEREOF

(75) Inventors: Paul J. Wang, Chestnut Hill, MA (US); Hassan Rastegar, Newton, MA (US)

(73) Assignee: New England Medical Center, Boston, MA (US)

( * ) Notice: Subject to any disclaimer, the term of this patent is extended or adjusted under 35 U.S.C. 154(b) by 155 days.

(21) Appl. No.: 09/710,284

(22) Filed: Nov. 10, 2000

(51) Int. Cl.[7] ............................................... A61B 18/14
(52) U.S. Cl. ............................ 604/41; 600/37; 607/96
(58) Field of Search .................... 600/37, 508, 204; 606/41, 27, 33, 205; 128/898; 607/101, 96

(56) References Cited

U.S. PATENT DOCUMENTS

| | | | |
|---|---|---|---|
| 5,156,151 A | 10/1992 | Imran | 128/642 |
| 5,330,501 A | 7/1994 | Tovey et al. | 606/198 |
| 5,396,887 A | 3/1995 | Imran | 128/642 |
| 5,400,783 A | 3/1995 | Pomeranz et al. | 128/642 |
| 5,427,119 A | 6/1995 | Swartz et al. | 128/772 |
| 5,443,463 A | 8/1995 | Stern et al. | 606/51 |
| 5,462,545 A | 10/1995 | Wang et al. | 606/41 |
| 5,496,312 A | 3/1996 | Klicek | 606/34 |
| 5,497,774 A | 3/1996 | Swartz et al. | 128/658 |
| 5,505,730 A | 4/1996 | Edwards | 606/41 |
| 5,536,267 A | 7/1996 | Edwards et al. | 606/41 |
| 5,555,883 A | 9/1996 | Avitall | 128/642 |
| 5,558,073 A | 9/1996 | Pomeranz et al. | 128/642 |
| 5,575,766 A | 11/1996 | Swartz et al. | 604/53 |
| 5,575,788 A | 11/1996 | Baker et al. | 606/41 |
| 5,575,810 A | 11/1996 | Swanson et al. | 607/99 |
| 5,595,183 A | 1/1997 | Swanson et al. | 128/697 |
| 5,617,854 A | 4/1997 | Munsif | 128/642 |
| 5,637,090 A | 6/1997 | McGee et al. | 604/95 |
| 5,673,695 A | 10/1997 | McGee et al. | 128/642 |
| 5,676,662 A | 10/1997 | Fleischhacker et al. | 606/41 |
| 5,687,723 A | 11/1997 | Avitall | 128/642 |
| 5,688,267 A | 11/1997 | Panescu et al. | 606/41 |
| 5,690,611 A | 11/1997 | Swartz et al. | 604/53 |
| 5,730,127 A | 3/1998 | Avitall | 128/642 |

(List continued on next page.)

FOREIGN PATENT DOCUMENTS

| | | |
|---|---|---|
| WO | WO 95/10318 | 4/1995 |
| WO | WO 95/10319 | 4/1995 |
| WO | WO 95/10320 | 4/1995 |
| WO | WO 95/10321 | 4/1995 |
| WO | WO 95/10978 | 4/1995 |
| WO | WO 96/10961 | 4/1996 |
| WO | WO 96/26675 | 9/1996 |
| WO | WO 96/39966 | 12/1996 |
| WO | WO 97/06727 | 2/1997 |
| WO | WO 97/17904 | 5/1997 |
| WO | WO 97/25916 | 7/1997 |
| WO | WO 97/25918 | 7/1997 |
| WO | WO 97/25919 | 7/1997 |
| WO | WO 97/32525 | 9/1997 |
| WO | WO 97/37607 | 10/1997 |
| WO | WO 97/45156 | 12/1997 |

OTHER PUBLICATIONS

Avitall et al., "A Thoracoscopic Approach to Ablate Atrial Fibrillation Via Linear Radiofrequency Lesion Generation on the Epicardium of Both Atria", (1996) Pace 19: 626.

(List continued on next page.)

*Primary Examiner*—Teresa Walberg
*Assistant Examiner*—Leonid M Fastovsky
(74) *Attorney, Agent, or Firm*—Testa, Hurwitz & Thibeault, LLP (57) ABSTRACT

A device for tissue ablation and a method of using the device.

22 Claims, 9 Drawing Sheets

U.S. PATENT DOCUMENTS

| | | | |
|---|---|---|---|
| 5,730,704 A | | 3/1998 | Avitall .......................... 600/374 |
| 5,733,280 A | | 3/1998 | Avitall ........................... 606/23 |
| 6,081,749 A | * | 1/2000 | Ingle et al. ................... 607/101 |
| 6,053,913 A | * | 4/2000 | Tu et al. ......................... 606/41 |
| 6,068,629 A | * | 5/2000 | Haissaguerre et al. ......... 606/41 |
| 6,071,303 A | * | 6/2000 | Laufer ........................... 607/96 |
| 6,139,492 A | * | 10/2000 | Vierra et al. ................. 600/204 |
| 6,152,143 A | * | 11/2000 | Edwards ..................... 128/898 |
| 6,159,207 A | * | 12/2000 | Yoon ............................. 606/41 |
| 6,197,022 B1 | * | 3/2001 | Baker ............................ 606/33 |
| 6,231,518 B1 | * | 5/2001 | Grabek et al. ............... 600/508 |
| 6,361,531 B1 | * | 3/2002 | Hissong ........................ 606/27 |
| 6,394,948 B1 | * | 5/2002 | Borst et al. .................... 600/37 |
| 2002/0032441 A1 | * | 3/2002 | Ingle et al. .................... 606/41 |
| 2002/0058934 A1 | * | 5/2002 | Wang et al. ................... 606/41 |

OTHER PUBLICATIONS

Chevalier et al., "Video–assisted Thoracoscopic Radio Frequency Catheter Ablation of the Left Atrium Prevents Inducibility of Atrial Fibrillation in Dogs", Circulation (1997) 96: 575.

Cox, J.L. et al., "The Surgical Treatment of Atrial Fibrillation. III. Development of a Definitive Surgical Treatment", J. Thorac Cardiovasc Surg. (1991) 101: 569–583.

Jais, P. et al., "Catheter Ablation of Paroxysmal Atrial Fibrillation: High Success Rates with Ablation in the Left Atrium", Circulation (1996) 94: I–675.

Lindsay et al., "Intraoperative Observation and Epicardial Mapping after Attempted Catheter Ablation of Atrial Fibrillation", Circulation (1997) 96: 450.

Nakagawa et al., "Use of Atrial Potential Attenuation to Identify Endpoint of Radiofrequency Application for Continuous Transmural Linear Atrial Ablation", Circulation (1997) 96: 577.

Lee et al., "Minimally Invasive Epicardial Atrial Linear Ablation Using Cooled Radiofrequency Energy", Circulation (1997) 96: 577.

Sharma et al., "A Comparison of Sequential with Simultaneous Delivery of RF Energy Application at Mulitple Electrodes to Produce Linear Continuous Lesions", Circulation (1997) 96: 576.

Sie et al., "Radiofrequency Ablation of Atrial Fibrillation in Patients Undergoing Valve Surgery", Circulation (1997) 96: 450.

Thomas et al., "An Endocardial Radiofrequency Ablative Technique for Cure of Atrial Fibrillation During Cardiac Surgery", Circulation (1997) 96: 450.

* cited by examiner

TISSUE FOLDING DEVICE FOR TISSUE ABLATION, AND METHOD THEREOF

FIELD OF THE INVENTION

The invention relates to the treatment of cardiac arrhythmia and more specifically treatment of cardiac arrhythmia by tissue ablation.

BACKGROUND OF THE INVENTION

Tachycardia is a type of cardiac arrhythmia and is a serious, oftentimes, fatal condition characterized by rapid, uncontrolled, and ineffective beating of the heart. Most tachycardia falls into one of two broad categories: ventricular tachycardia (hereinafter VT) and supraventricular tachycardia (hereinafter SVT). VT occurs in the lower chambers of the heart, the ventricles, and frequently leads to serious complications, including sudden cardiac death. Atrial fibrillation and flutter, forms of SVT, originate in the upper chambers of the heart, the atria, and often result in chest pain, fatigue and dizziness and, while generally not life-threatening, is a leading cause of stroke in the United States.

Currently, many cases of VT and SVT are treated by drugs that modify the electrical characteristics of the heart tissue. However, the drugs do not eliminate or may not completely control the arrhythmia. In many cases of sustained VT, implantable cardiac defibrillators are used which deliver powerful shocks to the heart when fibrillation is detected. Concurrent treatment with drugs is standard therapy and each implantation of a cardiac defibrillator, of which there may be more than one per patient, is very expensive.

Some forms of SVT are treated by endocardial ablation, a minimally invasive procedure. During endocardial ablation, a mapping catheter is passed through an artery or vein into the patient'heart to find the site(s) of the arrhythmogenic tissue, the tissue from which the tachycardia originates. This same catheter or a separate catheter is used to transmit sufficient energy to thermally damage the tissue either by heating or cooling.

In atrial fibrillation the regular pumping action of the atria is replaced by a disorganized, ineffective quivering caused by chaotic conduction of electrical signals through the upper chambers of the heart. Although not immediately life threatening, atrial fibrillation may cause up to a 30% reduction in cardiac output and can lead to more serious conditions, including the formation of blood clots in the atria that can dislodge and travel to the brain resulting in stroke. Currently, the only curative treatment for atrial fibrillation is the surgical "maze procedure", an open heart procedure in which the surgeon makes several incisions in the right and left atria creating scar tissue to electrically separate portions of the atria. Despite clinical success of the maze procedure, it is time-consuming and demanding. The procedure requires open-heart surgery and is very expensive. Accordingly, only a modest number of maze procedures are performed annually in a limited number of centers.

The present invention provides an apparatus and method for treating cardiac arrhythmia that may be widely applicable, generally, to ablation of tissues of other body systems, such as urogenital or gastrointestinal.

SUMMARY OF THE INVENTION

In one aspect of the invention, a gripper tissue ablator device includes at least one gripper arm, a tissue contacting surface, at least one ablation element, and a handle. The tissue contacting surface on the gripper arm contacts or nearly contacts the tissue surface. The tissue contacting surface of the gripper arm causes the tissue to "tent" or fold, drawing the folded tissue into contact with the ablation element. In a preferred embodiment, the gripper tissue ablator device is applied to cardiac tissue, such as the epicardial surface of the atrium, to ablate tissue. In other embodiments, the gripper tissue ablator device of the invention is applied to other tissue such as tissues of the urogenital tract, gastrointestinal system, or skin to ablate the tissue.

In yet another aspect, the invention relates to a method for ablating tissue. In one embodiment of this aspect of the invention, the gripper tissue ablator device is used to ablate tissue, preferably atrial tissue. In this embodiment, the epicardial surface of the heart is approached via a thoracotomy or thoracoscopy. The operator grasps the handle of the device and applies the ablation member on to the atrial tissue site to be ablated. Following the application of negative pressure to the tissue generated by a pump or syringe in communication with surface gripping elements, the device is moved in a direction substantially perpendicular to the tissue plane, pulling the tissue underlying the gripping elements in the same direction. By pulling the tissue underlying the gripping elements, the tissue "tents" by forming a fold or crease in the tissue in contact with the ablation member. As the tissue folds, the endocardial surface at the sides of the fold are drawn together. In one embodiment, the tissue is pulled upward into the ablation device, which applies ablation energy to the tissue that is "tented."Ablation energy to heat, freeze, or otherwise kill tissue, such as a cryogen, is applied to the ablation elements adjacent to the gripping elements on the tissue contacting surface of the ablation member to cause one or more myocardial ablative lesions.

In another embodiment of the method of the invention, a gripper tissue ablator device having more than one gripper arm is used. In this method of the invention, the operator approaches the tissue surface in the same manner as described above. The handle of the device is grasped by the operator and the gripper arms are applied to the surface of the epicardium. The tissue contacting surface of the gripper arms holds fast the tissue in contact with the tissue contacting surface by adhesion, friction, or suction. The gripper arms are moved toward one another to cause the tissue between the arms to tent. Alternatively, the ablation member is made from a flexible material. The operator grasps the ablation member and squeezes the ablation member to cause the tissue gripped by the ablation member to fold. The tissue in the fold is ablated by application of ablation energy, such as a radio-frequency energy to ablation elements disposed on the gripper arms, on the ablation member, or on both the ablation member and gripper arms.

BRIEF DESCRIPTION OF THE DRAWINGS

FIG. 2AA is a cross-sectional view of cross-section AA shown in FIG. 2A.

FIG. 2CC is a perspective sectional view of cross-section CC shown in FIG. 2A.

FIG. 4BB is a cross-sectional view of cross-section BB shown in FIG. 4B.

FIG. 6AA is a perspective cross-sectional view of cross-section AA shown in FIG. 6A.

DETAILED DESCRIPTION OF THE INVENTION

Figure 1A:
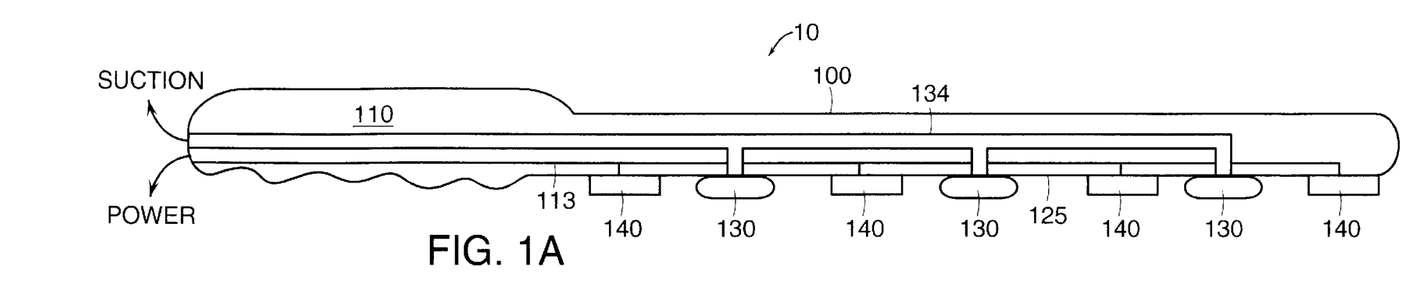
FIG. 1A is a cross-sectional view of one embodiment of a gripper tissue ablator device invention including a gripper arm.

Referring to FIG. 1A, in one embodiment, a gripper tissue ablator device 10 includes a handle 110, a gripper arm 100, a tissue contacting surface 125 on the gripper arm 100, one or more gripping elements 130, and one or more ablation elements 140. In one embodiment, the gripper arm in length is about 2.5–10 cm, preferably 3.5–7 cm, and the gripper arm in diameter is about 1–20 mm, preferably 3–9 mm. The surfacing gripping elements 130 can feature adhesive, corrugations, hooks, or suction elements, for example, or a combination of surface gripping elements that reversibly grip, i.e., hold fast tissue, thereby pinching, tenting, or folding the tissue in contact with the gripper surface 125 along the length of the gripper arm 100. In the embodiment shown, the gripping elements are suction elements 130. The suction elements 130 include one or more holes in the tissue contacting surface 125 of the gripper arm 100. The one or more holes of the suction elements 130 communicate with a tube 134 that runs through the interior of the long axis of the gripper arm 100. Negative pressure is applied within the tube 134 by an apparatus such as a pump, or a syringe in communication with the tube 134, to generate a vacuum at the tissue contacting surface 125 of the gripper arm 100.

Figure 1B:
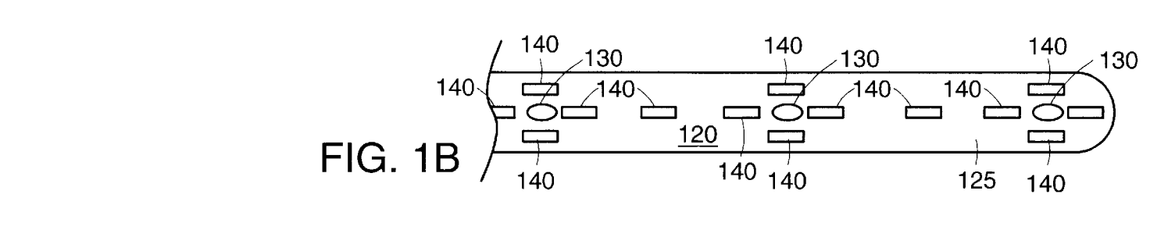
FIG. 1B is a plan view of a portion of the tissue contacting surface of the device illustrated in FIG. 1A.

One or more ablation elements 140 are distributed along the tissue gripping surface 125 of the gripper arm 100 in a linear or an array pattern as illustrated, for example, in FIG. 1B. Gripping elements 130 are arranged in the same pattern as the ablation elements 140 or in a different pattern than the ablation elements. The ablation elements 140 can be individually controlled, and are, for example, radio-frequency, direct current, or laser ablators. Power to the ablation elements 140 is supplied individually by conductors 113. In a particularly preferred embodiment, the ablation elements 140 are cooling elements, for delivery of cryogens to cool the tissue surface.

Figure 1C:
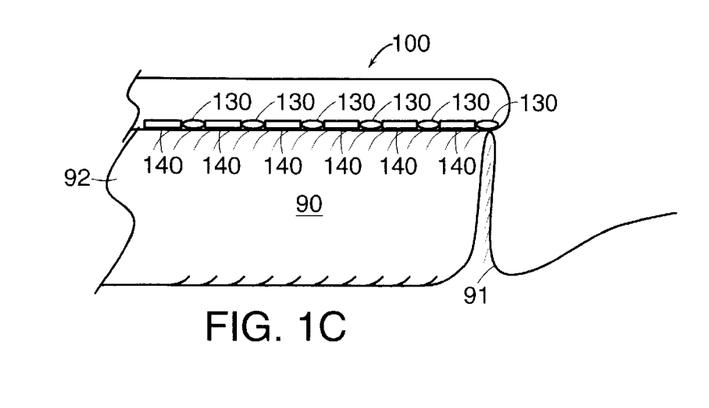
FIG. 1C is an illustration of a side-view of the gripper arm illustrated in FIG. 1A while the gripper arm grips and tents the tissue.

Referring now to FIG. 1C, when a vacuum is applied to the suction elements 130 and the suction elements 130 are brought in contact, or near contact with the tissue 90, the tissue 90 is reversibly bound to the suction elements 130 by the vacuum generated by the pump or syringe in communication with the suction elements 130. The tissue 90 is thereby drawn into contact with the ablation elements 140 adjacent the suction elements 130.

In operation, an operator grasps handles 110 of the device 10. As suction is applied via suction elements 130 to grip tissue 90, the gripper arm 100 is moved by the operator in a direction substantially perpendicular to the original plane of the tissue surface, as illustrated in FIG. 1C, viewed from the side of the gripper arm 100, and in FIG. 1D, viewed from the end of the gripper arm 100. As the gripper arm 100 is moved, the tissue 90 is pulled up into a fold or ridge 132 that extends between the points of contact of the suction elements 130 with the tissue 90, best illustrated in FIG. 1C.

Figure 1D:
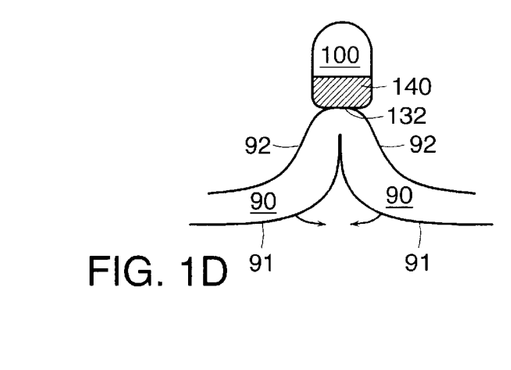
FIG. 1D is an end-view of the embodiment of the invention illustrated in FIG. 1C in use.

In a particularly preferred embodiment, the gripper tissue ablator device 10 is used to ablate a portion of the atrial wall 90. As the epicardial surface 92 is tented, as described above, the endocardial surfaces 91, deep to the epicardial surface 92, in contact with the gripper arm 100, best viewed in FIG. 1D, are drawn together. By folding or tenting the tissue 90 in this manner, the blood circulating within the heart chamber is no longer in contact with the tented tissue. By doing so, the warming effect of circulating blood is minimized which permits more efficient freezing of the atrial tissue 90 in the case of cryogenic ablators. Alternatively, the cooling effect of circulating blood is minimized, permitting more efficient heating of the atrial tissue.

Figure 2:
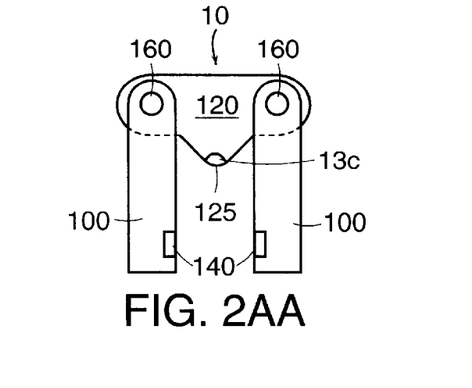
Figure 2A:
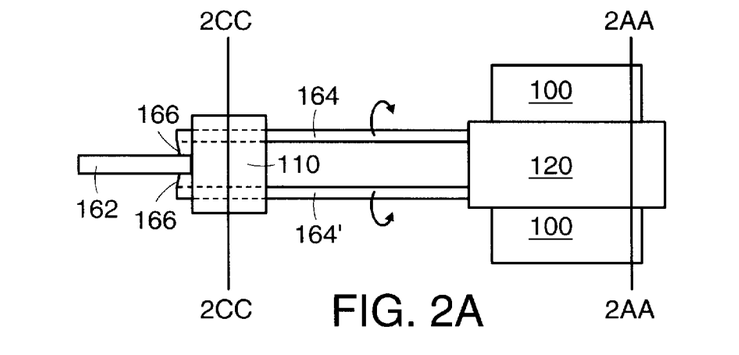
FIG. 2A illustrates a top-view of an embodiment of the invention including two gripper arms.
Figure 2B:
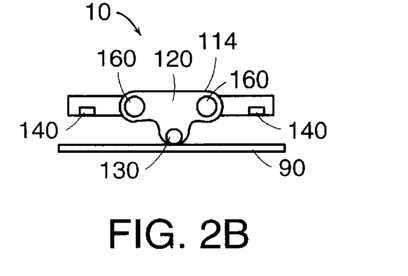
FIGS. 2B–2E illustrate a series of steps in ablating tissue viewed from the end of the gripper arm illustrated in FIG. 2A.

In another aspect of the invention, illustrated in FIGS. 2A and 2AA, the gripper tissue ablator device 10 includes a handle 110, at least two gripper arms 100, a member 120, a tissue contacting surface 125, at least one ablation element 140 and at least one surface gripping element 130. Each of the gripper arms 100 are pivotally joined to ablation member 120 by a pivot 160 such as a pin hinge or other pivoting mechanisms known to one skilled in the art. The surface gripping elements 130, such as suction elements 130, are positioned on the tissue contacting surface 125 of member 120. In one embodiment, illustrated in FIG. 2B as viewed from the distal end 114 of the device 10, ablation elements 140 are disposed on the tissue contacting surface 125 of one or both of the gripper arms 100.

Figure 2C:
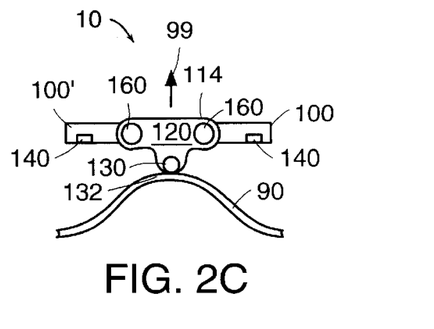
Figure 2D:
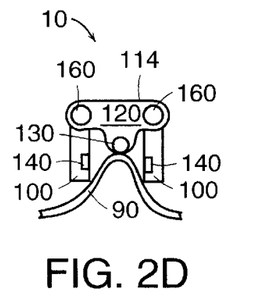
Figure 2E:
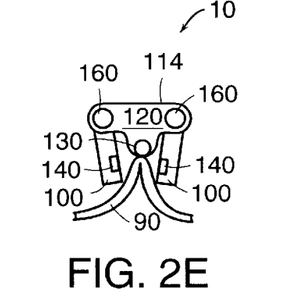

As shown in FIG. 2C, while negative pressure is applied to suction elements 130 on the tissue contacting surface 125 of the ablation member 120, the operator pulls device 10 away in a substantially perpendicular direction to the original tissue plane in the direction of the arrow 99, causing the tissue 90 to fold along a ridge 132. Referring to FIGS. 2D and 2E, gripper arms 100 are rotated about pivot 160 to bring the ablation elements 140 in contact with the folded tissue 90.

With reference to FIG. 2A, in one embodiment of the invention, control rod 162, rotating rods 164, 164', gears 166 are components of a mechanism for causing rotation of gripper arms 100. Control rod 162 is operably joined to rotating rods 164 and 164' via gear set 166. In one embodiment, gear set 166 includes four gears 167, 167', 167'', 167''' as illustrated in FIG. 2CC. Gear 167' is rotated in the direction indicated by arrow (a') by rotating control rod 162 in the direction indicated by arrow (a). Rotating rod 164, operably joined to gear 167 and gear 167', is rotated in the direction of arrow (e). Gear 167'', operably joined to gear 167', is rotated in the direction of arrow (c) and gear 167''' is rotated in the direction indicated by arrow (d). Rotating rod 164', operably joined to gear 167''', is rotated in the direction indicated by arrow (f). Rotation of rotating rods 164, 164', as indicated in FIG. 2CC, rotates gripper arms 100, 100', illustrated in FIG. 2A, to the position of gripper arms 100, 100' illustrated in FIG. 2AA.

Figure 2F:
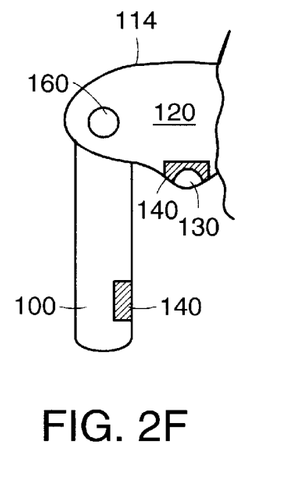
FIGS. 2F–2H illustrate embodiments of the member and gripper arm illustrated in FIG. 2AA.
Figure 2G:
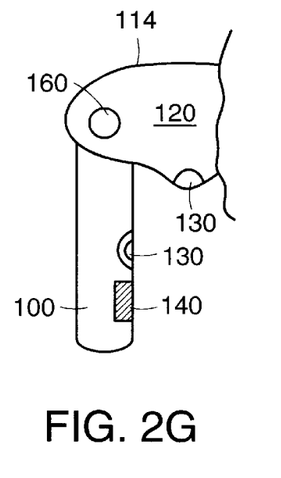
Figure 2H:
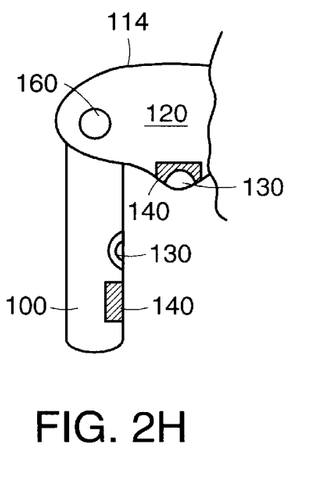

With reference to FIGS. 2F–2H, in alternate embodiments of this aspect of the invention, surface gripping elements 130 and ablation elements 140 may be disposed on either or both gripper arms 100 and member 120.

Figure 3A:
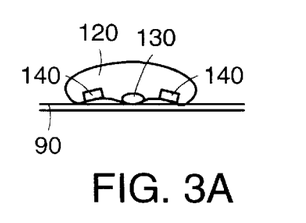
FIGS. 3A–3C illustrate another embodiment of the invention.
Figure 3B:
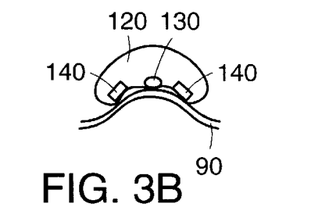
Figure 3C:
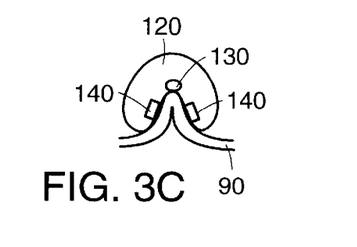
Figure 4:
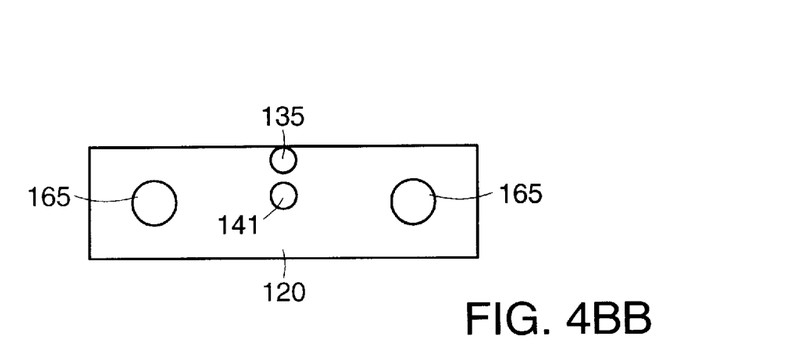
Figure 4A:
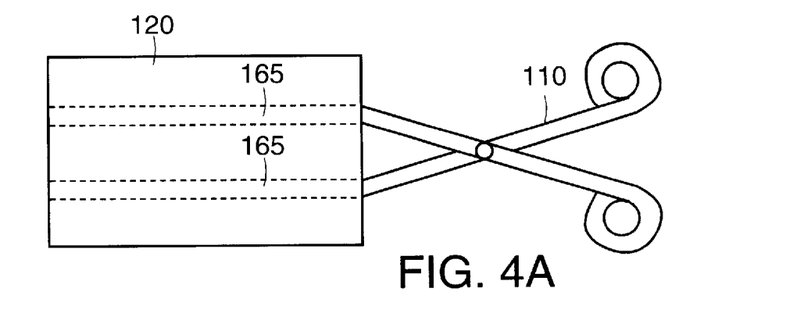
FIGS. 4A–4B illustrate an embodiment of the invention comprising rods.
Figure 4B:
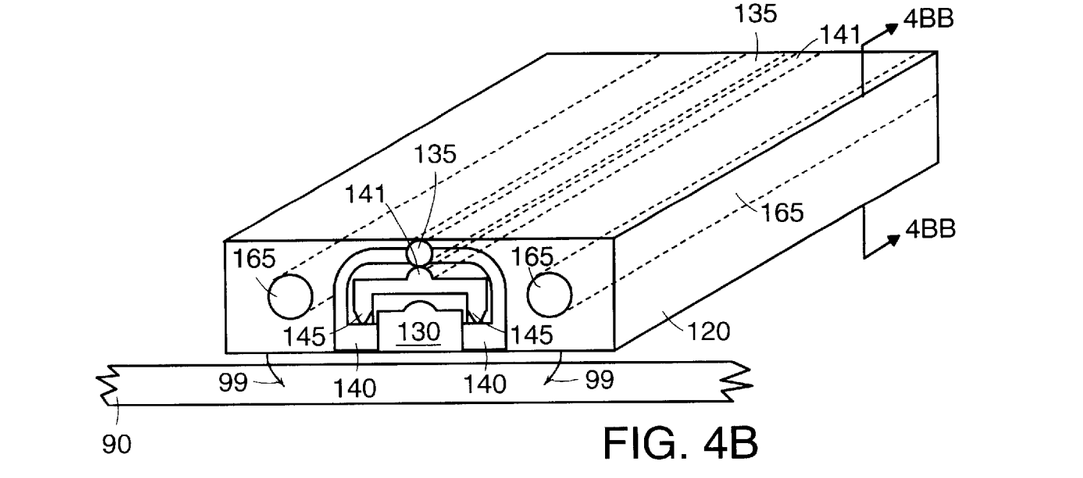

In another embodiment of the invention, illustrated in FIGS. 3A, 3B, and 3C, member 120 is made from a flexible material with memory such as plastic. The flexible sides of member 120 may be squeezed by the operator, as illustrated in FIGS. 3B and 3C, as tissue 90 is gripped by member 120 to cause tissue 90 to "tent". Alternatively, referring to FIGS. 4A, 4B and 4BB, a pair of rods 165, are axially positioned and embedded in the flexible material of member 120. Rods 165 are operably attached to handles 110, such as scissor type handles illustrated in FIG. 4A. Rods 165 are actuated by handles 110 to flex member 120 in the direction of arrows 99 to fold the tissue 90 in contact with suction element 130 and ablation elements 140. Cryogen exhaust tube 135, cryogen delivery tube 141, and cryogen nozzles 145 in contact with ablators 140, are embedded in member 120 and parallel rods 165, illustrated in FIGS. 4B and 4BB.

Figure 5A:
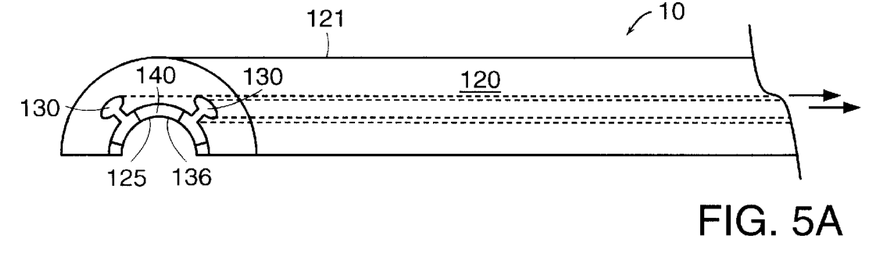
FIG. 5A illustrates another embodiment of the invention.

In an alternate embodiment of the invention, with reference to FIG. 5A, member 120 of the gripper tissue ablator device 10 features at least one cavity 136 on the tissue contacting surface 125. The cavity 136 is an excavated region of the tissue contacting surface 125 of member 120 and may extend along all or a portion of the tissue contacting surface 125 of member 120.

Figure 5B:
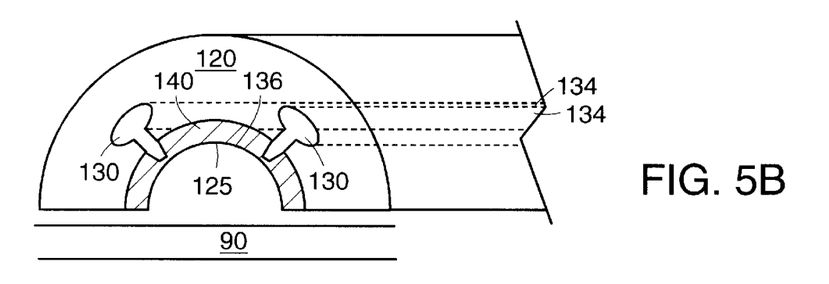
FIGS. 5B–5C illustrate a series of steps in ablating tissue according to the embodiment of the invention illustrated in FIG. 5A.

As shown in the perspective cross-section of a gripper arm 100 illustrated in FIG. 5B, ablation elements 140 and gripping elements 130 are disposed on the tissue contacting surface 125 of cavity 136. In operation, the operator grasps the handle of device 10 (not shown) and positions member 120 on tissue 90. Negative pressure is applied to suction elements 130 by a vacuum pump or other suitable means connected to suction elements 130 by tubes 134.

Figures 5C, 5D, 5E:
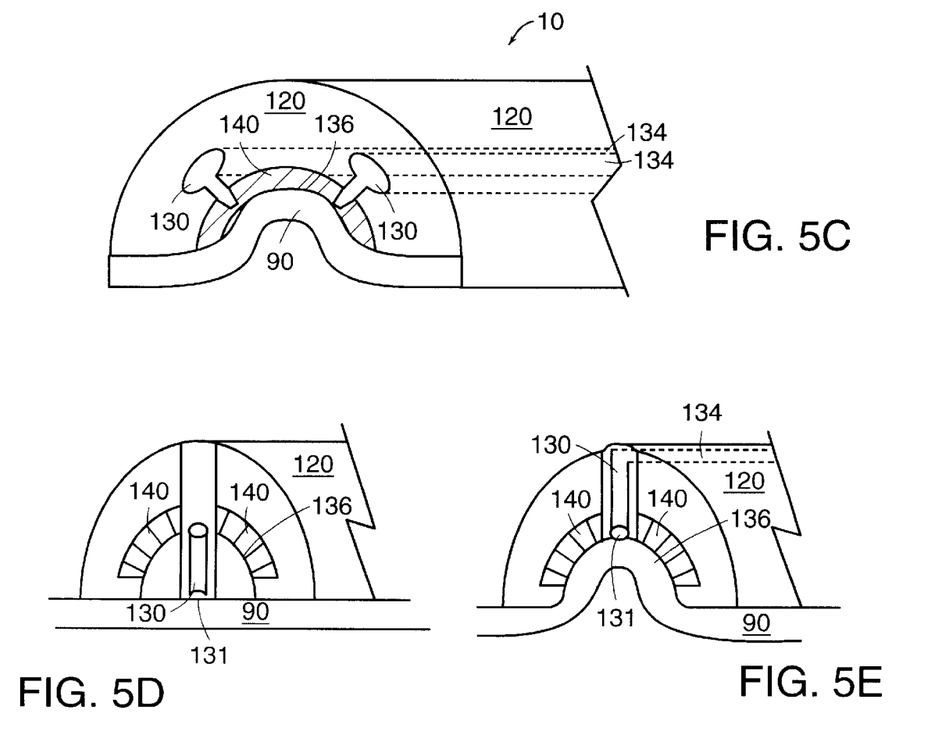
FIGS. 5D–5E illustrate the steps in ablating tissue with another embodiment of the invention.

With reference to FIG. 5C, as a vacuum is applied to suction elements 130, tissue 90 adheres to the tissue contacting surface 125 of the cavity 136 on member 120. Thus, tissue 90 is drawn into contact with ablation elements 140 by suction elements 130. Ablation energy, for example, microwaves are applied to the ablation elements 140 to ablate tissue 90 adhered to suction elements 130 and tissue contacting surface 125.

Alternatively, a central suction element 130, illustrated in FIG. 5D, extends downward from the tissue contacting surface of cavity 136 toward tissue 90 until the operative end 131 of the suction element 130 contacts tissue 90. A spring mechanism is used to pull the moveable suction element 130 downward. Negative pressure is applied to the suction element 130 by a vacuum pump or other suitable means connected to suction elements 130 by tubes 134. A pull wire is used to pull the suction elements upwards. As shown in FIGS. 5D and 5E, with suction applied to the tissue 90, the suction element 130 is withdrawn upwards into the ablation member 120 pulling the tissue 90 with it into cavity 136. Tissue 90 folds as it is drawn into cavity 136 and brought into contact with ablation elements 140 disposed on the tissue contacting surface of ablation member 120 as shown in FIG. 5E.

In an alternate embodiment, member 120 illustrated in FIG. 5A is made of a plastic or plastic/metal composite with memory so that member 120 may be flattened against tissue surface 90 by applying downward pressure or force perpendicular to member 120 on its surface 121. Suction is applied to gripping elements 130 and the downward force is removed causing memory material member 120 to pull tissue 90 upward in a direction substantially perpendicular to the original tissue plane. In yet another embodiment, rods 165, similar to rods 165 illustrated in FIGS. 4A–4B, may be embedded in member 120 and used to flatten member 120 against tissue surface 125.

Figure 6:
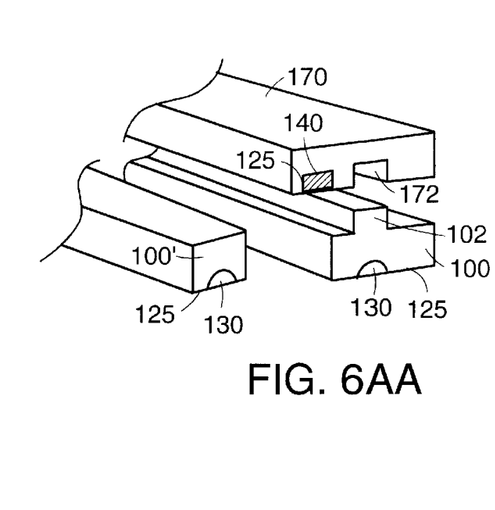
Figure 6A:
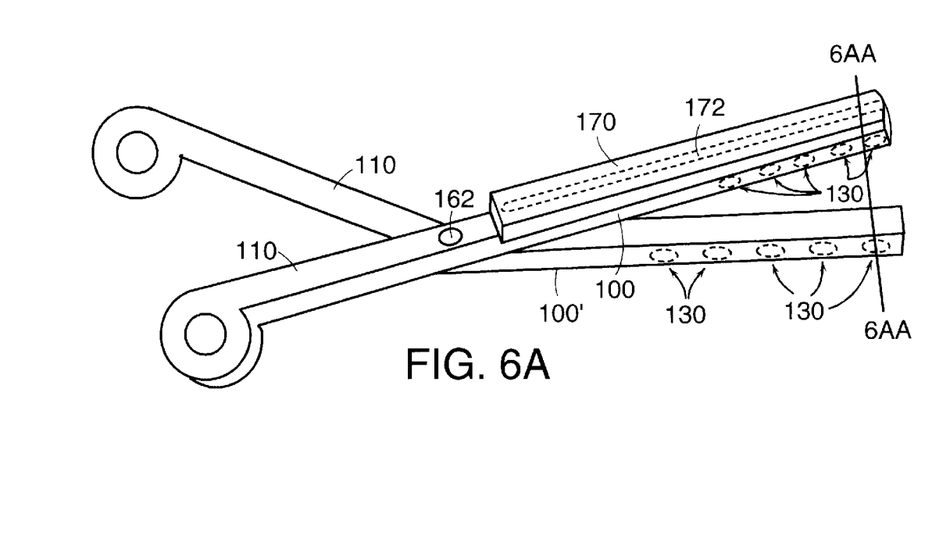
FIG. 6A illustrates another embodiment of the gripper tissue ablator device according to the invention.

Another embodiment of the invention is a system featuring two gripper arms 100, 100', a pivot 162, a handle 110, and an ablator tube 170, as illustrated, for example, in FIG. 6A and FIG. 6AA. Referring to FIG. 6AA, at least one of the gripper arms 100 includes a ridge 102 that runs longitudinally along all or a portion of the gripper arm 100 on the surface of one side of gripper arm 100 other than the side of the gripper arm 100 that is in contact with the tissue preferably the side opposite to the tissue contacting surface. Surface gripping elements such as suction elements 130 may be disposed on the tissue contacting surface 125 of gripper arms 100, 100'.

The ablator tube 170, illustrated in FIG. 6AA, has a groove 172 that is complementary to ridge 102 on the gripper arm 100. One or more ablation elements 140 are disposed adjacent to groove 172 on the tissue contacting surface 125 of the ablation tube 170.

Figures 6B, 6D:
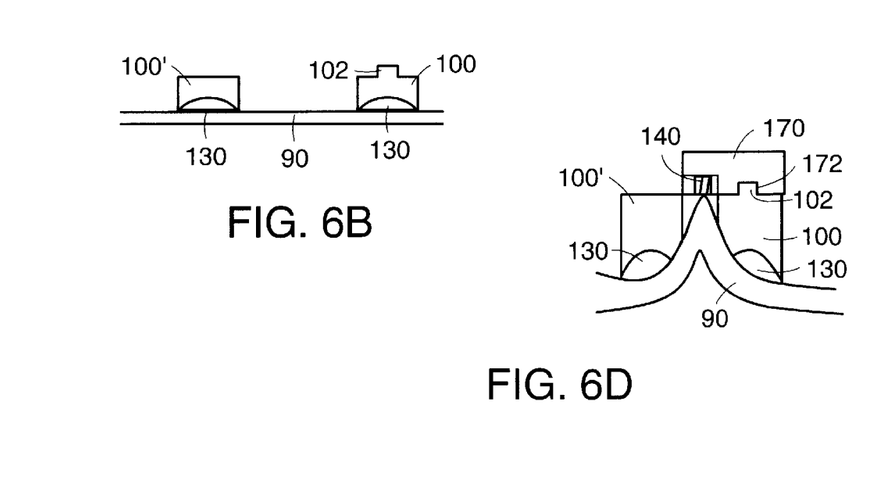
FIG. 6B illustrates an end-view of an embodiment of the gripper tissue ablator device illustrated in FIG. 6A in the open position.
FIG. 6D illustrates an end-view of an embodiment of the device illustrated in FIG. 6B including the ablator tube.
Figure 6C:
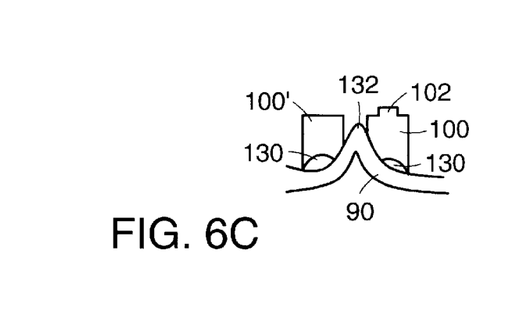
FIG. 6C illustrates an end-view of an embodiment of the gripper tissue ablator device illustrated in FIG. 6B in the closed position.

Alternatively, groove 172 is disposed on the gripper arm 100 and ridge 102 is positioned on the ablation tube 170. Thus, gripper arms 100, 100' are placed in an open position, as illustrated in FIG. 6B, on tissue 90. Negative pressure is applied to suction elements 130 to "grip" tissue 90. Gripper arms 100, 100' are pivoted to the closed position illustrated in FIG. 6C, by actuating handles 110. By moving gripper arms 100, 100' from the open position illustrated in FIG. 6B to the closed position illustrated in FIG. 6C, tissue 90 is folded along a ridge 132. The groove 172 of ablation tube 170 is slid or snapped on complementary ridge 102 of the gripper arm 100 as shown in FIG. 6D. Ablation elements 140 contact the folded tissue 90 and ablation energy is applied to the tissue 90.

Figure 7A:
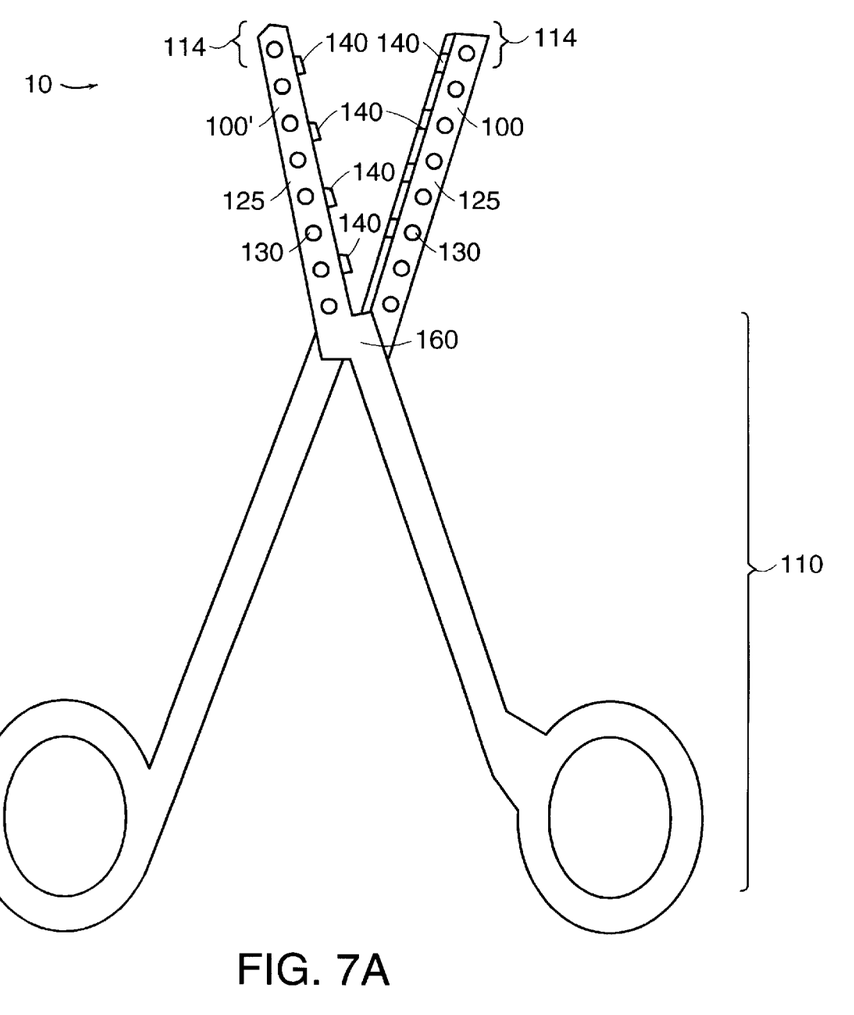
FIG. 7A illustrates an embodiment of a scissor-type gripper tissue ablator device according to the invention.

Alternatively, an embodiment of this aspect of the invention includes a "scissor" type gripper tissue ablator device. Referring to FIG. 7A, this embodiment features a scissor-type handle 110, a pivot 160, at least two gripper arms 100, 100', at least one surface gripping element 130, and at least one ablation element 140.

The two gripper arms 100 of the "scissor" type gripper tissue ablator device are operatively joined to the handle 110 via a pivot 160. Operation of the 10 handle 110 causes the gripper arms 100, 100' to rotate about the pivot. In the "open" position illustrated in FIG. 7A, the gripper arms 100 are parted at the distal end 114 of the device 10. In the "closed" position illustrated in FIG. 7B from the end of the device 10, the gripper arms are touching or nearly touching at the distal end 114 of the device 10.

Figure 7B:
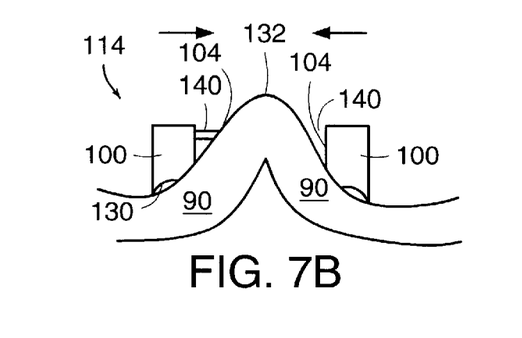
FIG. 7B illustrates an end-view of an embodiment of the device illustrated in FIG. 7A.

To operate this embodiment of the invention, the gripper arms 100 are moved from the "open" position illustrated in FIG. 7A to the "closed" position illustrated in FIG. 6B by operating the handles pivotally joined to the gripper arms 100 to move the gripper arms 100, 100' in the direction of the arrows illustrated in FIG. 7B. As the gripper arms 100, 100' move toward one another, the tissue is "pinched" to form a fold of tissue. Ablation elements 140 contact the sides of the tissue fold and the tissue 90 is ablated when ablation energy is applied to the ablation elements. Gripping element 130 is used to grip surface 90.

Figure 8A:
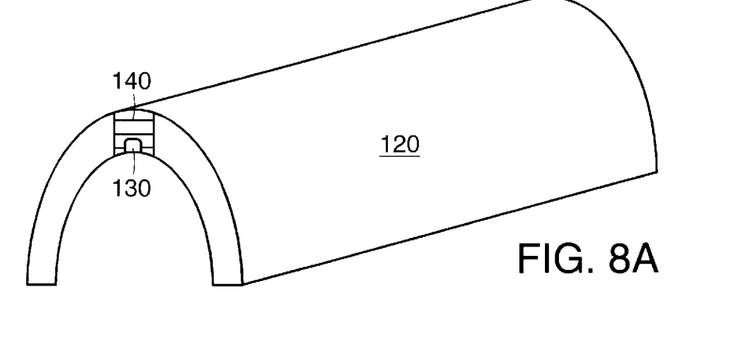
FIG. 8A illustrates an embodiment of the gripper tissue ablator device according to the invention.

In yet another embodiment, illustrated in FIG. 8A, member 120 features a flexible, substantially semi-circular or U-shape. Member 120 is made of one or more flexible materials such as flexible plastic, polyurethane, polyethylene, or silicone. Suction elements 130 and ablation elements 140 are disposed along tissue contacting surface 125.

Figure 8B:
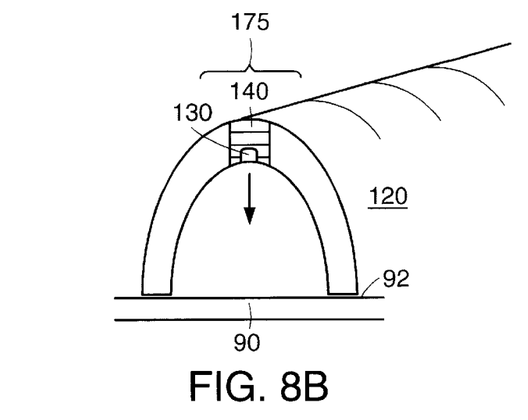
FIGS. 8B–8E illustrate a series of steps in ablating tissue according to the invention.
Figure 8C:
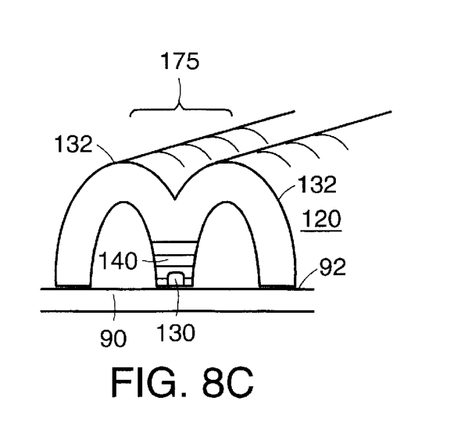
Figure 8D:
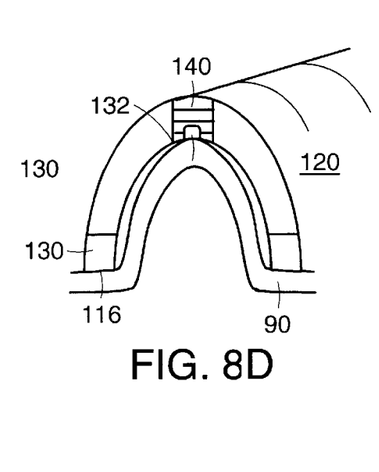

To operate the flexible member 120, member 120 is placed on the tissue 90, as illustrated in FIG. 8B. The midsection 175 of member 120 is manually pressed down by the operator in the direction of the arrow toward tissue surface 92. Gripping elements 130 contact the tissue surface 92. When negative pressure is applied to the gripping elements 130, tissue surface 92 is adhered to the gripping elements 130 on tissue contacting surface 125 of member 120. Upon release of mid-section 175 by withdrawing manual pressure, mid-section 175 returns to its original configuration, as illustrated in FIG. 8D, causing the tissue 90, adhered to gripping elements 130, to be drawn up with the gripping elements 130 in a direction substantially perpendicular to the original tissue plane. A fold 132 is introduced into tissue 90 that is drawn up with the suction element 130. Ablation energy is applied to ablation elements 140 to ablate the tissue 90.

Figure 8E:
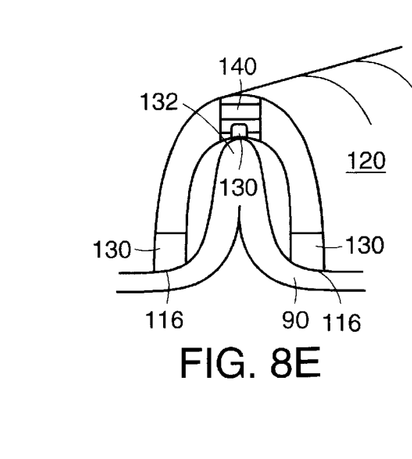

Another feature of this embodiment of the invention includes additional gripper elements disposed along the ends 116 of the U-shaped ablation member 120 as illustrated in FIG. 8D. Gripper elements 116 are squeezed together to further reduce blood flow to folded tissue 132 as shown in FIG. 8E.

Variations, modifications, and other implementations of what is described herein will occur to those of ordinary skill in the art without departing from the spirit and scope of the invention as claimed. Accordingly, the invention is to be defined not by the preceding description by instead by the spirit and scope of the following claims.

What is claimed is:

1. A method for ablation of cardiac tissue, comprising the steps of:
    contacting a device for cardiac ablation with said cardiac tissue; said device comprising an ablation element and a surface gripping element for folding said tissue and for contacting said tissue with said ablation element;
    gripping said cardiac tissue with said gripping element;
    folding said cardiac tissue gripped with said gripping element;
    applying ablation energy to said ablation element; and,
    ablating said cardiac tissue.

2. The method of claim 1 wherein said folding step further comprises applying negative pressure to said cardiac tissue through at least one suction element.

3. The method of claim 1 wherein said gripping step comprises the application of friction to said tissue.

4. The method of claim 1 wherein said ablating step comprises cryogenic ablation.

5. A device for ablation of cardiac tissue, comprising:
    a handle;
    at least one ablation element; and
    at least one gripper arm, said gripper arm comprising tissue gripping elements for folding said tissue and for contacting said tissue fold with said ablation elements.

6. The device of claim 5 further comprising an ablation member, wherein said at least one ablating element is disposed on said ablation member.

7. The device of claim 5 wherein said at least one ablation element is disposed on said at least one gripper arm.

8. The device of claim 5 wherein said tissue gripping element comprises at least one suction element.

9. The device of claim 8 wherein said suction element is disposed on said ablation member.

10. The device of claim 8 wherein said suction element is disposed on said at least one gripper arm.

11. The device of claim 5 comprising two gripper arms.

12. The device of claim 6 further comprising a pivot wherein said at least one gripper arm is pivotally joined to said ablation member.

13. The device of claims 6 wherein said ablation member comprises a flexible material.

14. The device of claim 5 wherein said ablation element comprises a cryogenic ablator.

15. The device of claim 5 wherein said cardiac gripping surface of said gripper arm comprises at least one cavity, said cavity comprising a plurality of ablation elements.

16. The device of claim 15 wherein said cavity parallels the long axis of said gripper arm.

17. The device of claim 15 further comprising at least one suction element disposed in said cavity.

18. The device of claim 15 wherein said ablation elements comprise cryogenic ablators.

19. The device of claim 15 further comprising a moveable suction element.

20. A system for ablation of cardiac tissue, comprising:
    at least two gripper arms, one of said gripper arms comprising a ridge;
    an ablation tube comprising a tissue contacting surface and a groove for interfacing with said ridge on said gripper arm; and
    at least one ablation element disposed on the tissue contacting surface of said ablation tube, wherein said at least two gripper arms grip said tissue to cause a tissue fold, and said ablation element on said ablation tube contacts said tissue fold to ablate said tissue.

21. The device of claim 20 further comprising at least one suction element disposed on at least one of said two gripper arms.

22. The device of claim 20 wherein said ablation elements comprise cryogenic ablators.

* * * * *